US00PP30361P2

(12) United States Plant Patent
Lommerse

(10) Patent No.: US PP30,361 P2
(45) Date of Patent: Apr. 9, 2019

(54) ***STEVIA* PLANT NAMED 'LOSTE1517'**

(50) Latin Name: ***Stevia rebaudiana* (Bertoni) Bertoni**
Varietal Denomination: LOSTE1517

(71) Applicant: Lommerse Holding BV, Mariahout (NL)

(72) Inventor: Henry Lommerse, Mariahout (NL)

(73) Assignee: Lommerse Holding B.V., Mariahout (NL)

( * ) Notice: Subject to any disclaimer, the term of this patent is extended or adjusted under 35 U.S.C. 154(b) by 0 days.

(21) Appl. No.: 15/932,173

(22) Filed: Feb. 15, 2018

(51) Int. Cl.
*A01H 5/00* (2018.01)

(52) U.S. Cl.
USPC ..... Plt./258

(58) Field of Classification Search
USPC ..... Plt./258, 263.1
See application file for complete search history.

*Primary Examiner* — Annette H Para
(74) *Attorney, Agent, or Firm* — Samuel R. McCoy, Jr.

(57) ABSTRACT

A new and distinct *Stevia* cultivar named 'LOSTE1517' which is characterized by the combination of a compact plant size, vigorous growth, improved cold tolerance, a high concentration sweetening compounds in the foliage, and the stability of these characteristics from generation to generation.

3 Drawing Sheets

Latin name of the genus and species: The Latin name of the genus and species of the novel variety disclosed herein is *Stevia rebaudiana* (Bertoni) Bertoni.

Variety denomination: The inventive cultivar of *Stevia* disclosed herein has been given the variety denomination 'LOSTE1517'.

BACKGROUND OF THE INVENTION

Parentage: The *Stevia* cultivar 'LOSTE1517' is the result of a planned breeding program carried out by the inventor at his greenhouse in Mariahout, the Netherlands. In May of 2013, the inventor performed a controlled cross-pollination of the seed parent, *Stevia* '3662/12' (not patented), with *Stevia* '3668/12' (not patented), the pollen parent. In March of 2014, a seedling that exhibited potential commercial value was selected from all other progeny. The seedling was given the reference code "5998/14" and allowed to grow to a mature size, for further evaluation. In the summer of 2014, the candidate was asexually propagated using softwood cuttings to assess the stability of the unique characteristics for which the candidate was originally selected. In April of 2015, a final selection was made and the new cultivar was given the name 'LOSTE1517'.

Asexual Reproduction: Asexual reproduction of 'LOSTE1517', by way of softwood stem cuttings, was first performed in the summer of 2014 at the inventor's greenhouse in Mariahout, the Netherlands and has since been further cloned using meristematic tissue culture propagation. Through five subsequent generations, the unique features of this cultivar have proven to be stable and true to type.

SUMMARY OF THE INVENTION

The cultivar 'LOSTE1517' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LOSTE1517'. These characteristics in combination distinguish 'LOSTE1517' as a new and distinct *Stevia* cultivar:

1. *Stevia* 'LOSTE1517' exhibits a compact growth habit; and
2. *Stevia* 'LOSTE1517' exhibits vigorous growth and free branching; and
3. *Stevia* 'LOSTE1517' exhibits foliage with a high tolerance to cold temperatures; and
4. *Stevia* 'LOSTE1517' exhibits foliage with a high concentration of steviol glycosides.

BOTANICAL DESCRIPTION OF THE PLANT

Figure 1:
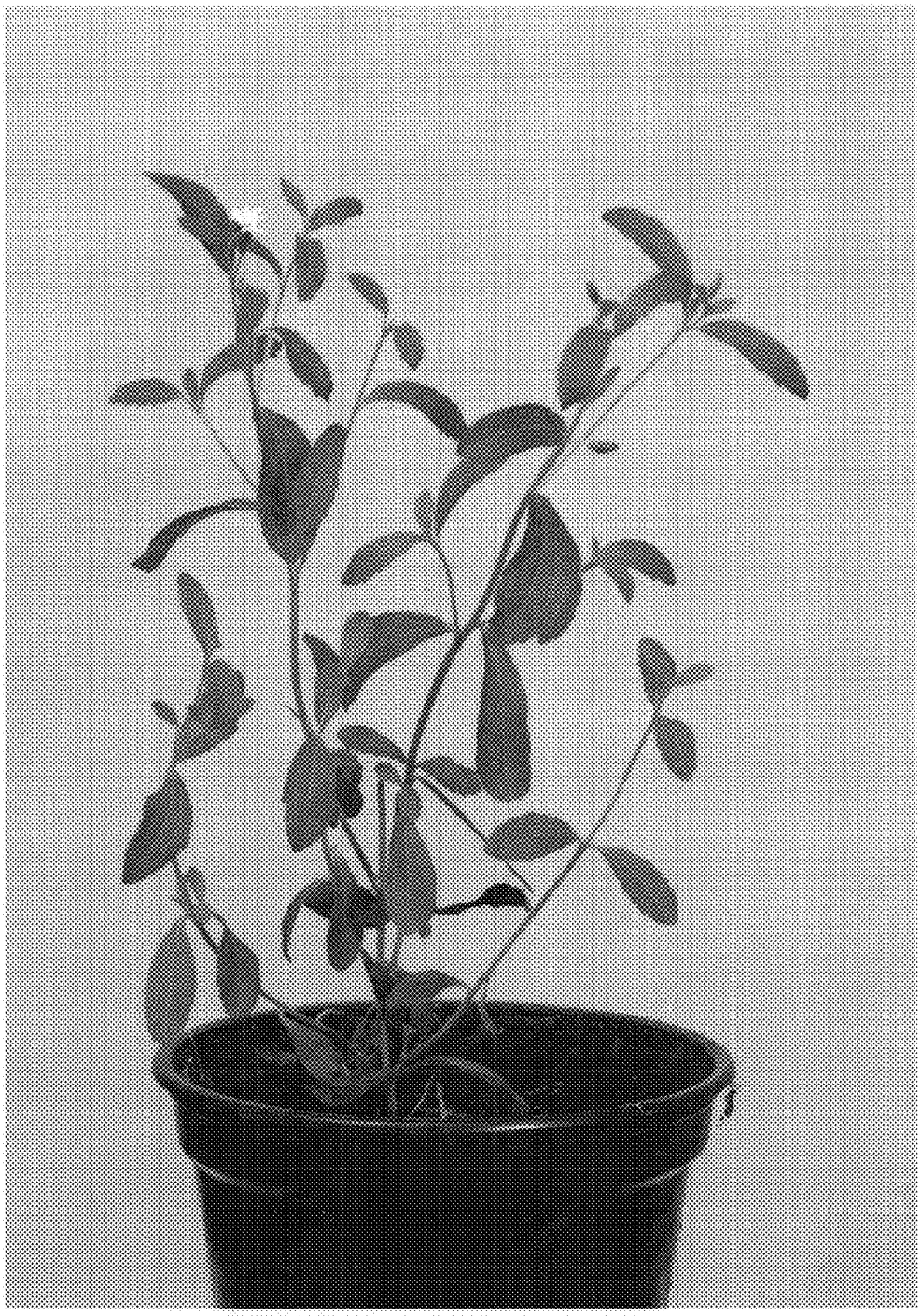
FIG. 1 illustrates, as nearly true as it is reasonably possible to make the same in color photographs of this type, an exemplary plant of 'LOSTE1517' grown in a greenhouse in Mariahout, the Netherlands. This plant, grown in an 11 cm nursery container, is approximately 8 weeks old from a rooted young plant.
Figure 2:
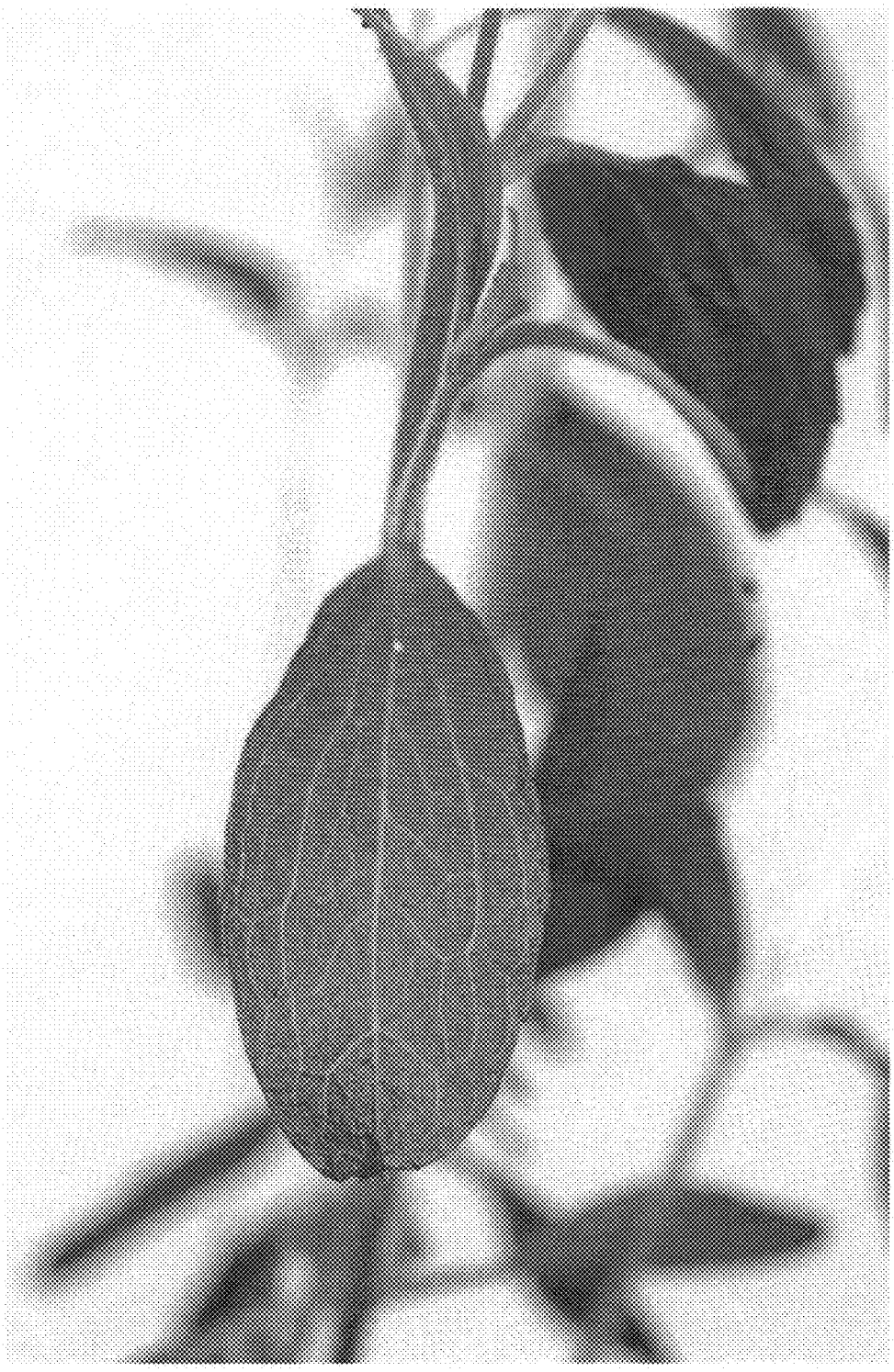
FIG. 2 illustrates, as nearly true as it is reasonably possible to make the same in color photographs of this type, the typical foliage of 'LOSTE1517'.
Figure 3:
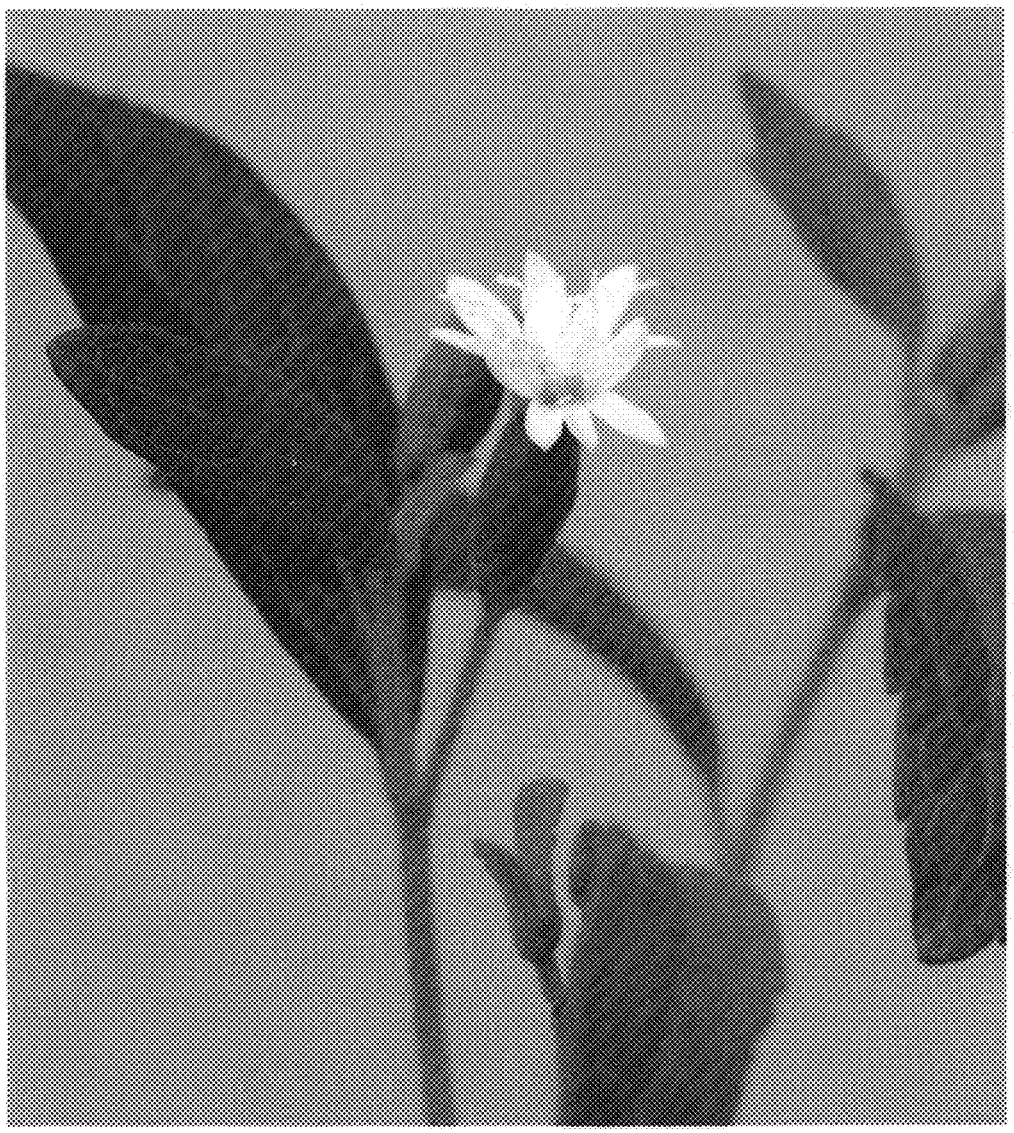
FIG. 3 illustrates, as nearly true as it is reasonably possible to make the same in color photographs of this type, the typical inflorescence and flowers of 'LOSTE1517'.

With the exception of the inflorescence and flower descriptions, the following observations and measurements made in January of 2018 describe averages from a sample set of six specimens of 8 week old 'LOSTE1517' plants grown in 11 cm nursery pots in a greenhouse in Mariahout, the Netherlands. Plants were produced without supplemental light, under shade cloth, using drip irrigation at regular intervals, and fertilized as required using a fertilizer with an analysis of 18-18-18-5. No chemical treatments of any kind were utilized.

Those skilled in the art will appreciate that certain characteristics will vary with older or, conversely, with younger plants. 'LOSTE1517' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'LOSTE1517' and comparisons with the parent plants and most similar commercial *Stevia* cultivar known to the inventor are provided below.

Plant description:

*Growth habit*.—Perennial; broad upright.

*Plant shape*.—Compact, ovate.

*Average height from base to top of foliage*.—22.0 cm.

*Average height from base to top of the floral plane*.—21.7 cm.

*Average spread*.—Average of 13.1 cm.

*Growth rate*.—Moderate.

*Plant vigor*.—Moderate.

*Propagation details*.—Asexual propagation is accomplished by both softwood stem cuttings and also by mericloning.

*Time to initiate roots*.—After deflasking the micropropagule, approximately 15 days are required for the propagule to initiate roots at 20 degrees Celsius.

*Time to produce a marketable* 17 *cm potted plant*.—Approximately 14 weeks.

*Disease and pest resistance or susceptibility*.—Neither resistance nor susceptibility to typical *Stevia rebaudiana* pests and diseases has been observed.

*Environmental tolerances*.—Adapt to at least USDA Zones 11 and 12 and temperatures as high as 40 degrees Celsius; moderate tolerance to rain; low tolerance to wind.

Root system:

*General*.—Moderately dense rooting.

*Dimensions, mature roots*.—18.0 cm long with a diameter of 0.1 cm, on average.

*Texture*.—Non-fleshy; slightly fibrous.

*Color*.—Greyed-yellow, nearest to a mixture of RSH 161B and 161C.

Stems:

*Branching habit*.—Main stems grow from the base, freely branching with lateral branches.

*Number of main stems per plant*.—1.

*Number of lateral branches per plant*.—6.

*Appearance and shape*.—Rounded.

*Length of lateral branches*.—11.9 cm.

*Diameter of lateral branches*.—Averaging 0.175 cm at the widest point.

*Internode length on lateral branches*.—3.5 cm.

*Luster*.—Moderately glossy.

*Attitude of lateral branches*.—Average angle is approximately 30 degrees from vertical.

*Strength*.—Moderately strong.

*Color, juvenile*.—Yellow-green, RHS 144A.

*Color, mature*.—Yellow-green, RHS 144A.

*Color at internodes*.—Yellow-green, RHS 144A.

*Color of oldest wood*.—Yellow-green, a mixture of RHS 146C and 146D.

*Pubescence*.—Stems are densely covered with a soft pubescence; average length of hairs is 0.1 cm; hairs are colored white to green-white, a mixture of RHS NN155B and 157D.

Foliage:

*General description*.—Foliage is edible with a very sweet taste due to the high concentration of steviosides.

*Arrangement*.—Opposite.

*Division*.—Simple.

*Number of leaves per lateral branch*.—8.

*Lamina*.—Dimensions — 4.6 cm long and 1.6 cm wide, on average. Shape — Oblanceolate to obovate. Aspect — Slightly curved downwards. Apex — Acute to bluntly acute. Base — Long attenuate. Margin — Serrate. Pubescence, adaxial surface — Moderately to densely covered with very short appressed hairs to approximately 0.3 mm in length; hairs colored white to green-white, RHS NN155B to 157D. Texture and luster of adaxial surface — Slightly glossy. Pubescence, abaxial surface — Moderately to densely covered with very short hairs to approximately 0.3 mm in length; hairs colored white to green- white, a mixture of RHS NN155B and 157D. Texture and luster of abaxial surface — Very slightly glossy. Color — Juvenile foliage, adaxial surface — Green, nearest to a mixture of RHS 137B and 137C. Juvenile foliage, abaxial surface — Green, RHS 137D. Mature foliage, adaxial surface — Nearest to in between green, RHS NN137A, and yellow-green, RHS 147A. Mature foliage, abaxial surface — Yellow-green, RHS 147B. Venation — Pattern — Pinnate. Color, adaxial surface — Yellow-green, RHS 146B. Color, abaxial surface — Yellow-green, RHS 146B.

*Sheath*.—Not sheathing.

*Petiole*.—Length — Average of 0.25 cm. Width — Petioles are flattened; average horizontal width is 0.2 cm and the average vertical width is 0.125 cm. Texture — Pubescent. Moderately covered with very short hairs to approximately 0.3 mm in length; hairs colored white to green-white, a mixture of RHS NN155B and 157D. Luster — Slightly glossy. Strength — Moderately strong. Color, adaxial surface — Yellow-green, RHS 144B. Color, abaxial surface — Yellow-green, RHS 144B.

*Dry weight of glycosides*.—Stevioside — 38.4 mg/g. Rebaudioside A — 59.8 mg/g. Others — 8.6 mg/g. Total steviol glycosides — 106.8 mg/g.

Inflorescence:

*Inflorescence arrangement*.—Terminally and axially borne capitula in a compound cyme.

*Natural flowering season*.—Autumn into winter.

*Time to flower*.—10 months.

*Quantity of flowers per inflorescence*.—1 capitula, axially or terminally.

*Quantity of flowers per plant*.—1 capitula.

*Quantity of flower buds per plant*.—9 capitula.

*Quantity of flowers and flower buds per plant*.—10 capitula.

*Inflorescence height*.—1.2 cm.

*Inflorescence diameter*.—1.0 cm.

*Peduncle*.—Length — 0.6 cm. Diameter — 0.08 cm. Strength — Moderately strong. Texture — Moderately to densely covered with a soft pubescence;

hairs with an average length of 0.1 cm; colored green-white, nearest to RHS 157D. Luster — Matte. Color — Yellow-green, RHS 144B.

Flower buds:

*Shape*.—Oblanceolate.

*Height*.—0.6 cm.

*Diameter*.—0.1 cm.

*Texture*.—Moderately pubescent with very short hairs, colored yellow-green, nearest to RHS 145D.

*Luster*.—Matte.

*Color*.—Yellow-green, nearest to RHS 145C.

Flower:

*Flower type*.—Composite; capitula.

*Flowering habit*.—Moderately flowering.

*Aspect*.—Upright to slightly outward.

*Fragrance*.—None.

*Flower longevity*.—One week, on average.

*Persistence*.—Persistent.

*Disc diameter*.—0.15 cm.

*Receptacle shape*.—Inverted triangular.

*Receptacle height*.—0.05 cm.

*Receptacle diameter*.—0.05 cm.

*Receptacle color*.—Yellow-green, nearest to RHS 144A.

*Ray florets*.—None present.

*Disc florets*.—Quantity of florets per capitula — Five. Shape — Tubular. Arrangement — Radial symmetry; one whorl; florets are unfused. Attitude — Upright. Length — 1.0 cm. Diameter, including stigmas — 0.6 cm, on average. Diameter, excluding stigmas — 0.5 cm, on average. Color, upper and lower surfaces — White, in between RHS 155C and 155D. Apex — Acute. Base — Fused into a tube. Margin — Entire; not undulated. Texture and luster, upper surface — Smooth, velvety and matte. Texture and luster, lower surface — Smooth, velvety and matte. Color, when opening, upper surface — White, nearest to NN155D; throat is yellow-green, nearest to RHS 150D; tube is colored slightly darker, nearest to a mixture of RHS 145B and 145C. Color, when opening, lower surface — White, nearest to NN155D; throat is yellow-green, nearest to RHS 150D; tube is colored slightly darker, nearest to a mixture of RHS 145B and 145C. Color, when fully opened, upper surface — White, nearest to NN155D; throat is yellow-green, nearest to RHS 150D; tube is colored slightly darker, nearest to a mixture of RHS 145B and 145C. Color, when fully opened, lower surface — White, nearest to NN155D; throat is yellow-green, nearest to RHS 150D; tube is colored slightly darker, nearest to a mixture of RHS 145B and 145C. Venation, when fully opened, upper surface — White, nearest to NN155C; throat is yellow-green, nearest to RHS 150D; tube is colored slightly darker, nearest to RHS 145B. Venation, when fully opened, lower surface — White, nearest to NN155C; throat is yellow-green, nearest to RHS 150D; tube is colored slightly darker, nearest to RHS 145B.

*Involucre; phyllaries*.—Arrangement — Rotate; one whorl around the disc. Quantity — Five. Length — 0.7 cm. Width — 0.2 cm. Shape — Narrow elliptic. Apex — Acute. Base — Cuneate. Margin — Entire. Texture, upper surface — Very sparsely pubescent; average length of hairs is 0.05 cm; color is green-white, nearest to RHS 157D. Texture, lower surface —Moderately pubescent; average length of hairs is 0.05 cm; color is green-white, nearest to RHS 157D. Luster, upper surface — Matte. Luster, lower surface — Matte. Color, upper surface — Green, RHS 138A. Color, lower surface — Green, RHS 138A.

*Pedicels*.—Length — 0.2 cm. Diameter — 0.08 cm. Attitude; angle to the peduncle — 15 degrees. Strength — Moderately strong. Texture — Densely covered with a soft pubescence; hairs with an average length of 0.1 cm; color of hairs is green-white, nearest to RHS 157D. Luster — Matte. Color — Yellow-green, RHS 146B.

Reproductive organs:

*Androecium*.—Stamen quantity — 5. Filament length — 0.3 cm. Filament color — Yellow-green, nearest to RHS 145D. Anther shape — Linear. Anther length — 0.15 cm. Anther width — 0.03 cm. Anther color — Yellow-green, nearest to RHS 153D. Pollen, presence — Low. Pollen color — Yellow, nearest to 11D.

*Gynoecium*.—Pistil quantity — One. Pistil length — 0.7 cm. Style length — 0.5 cm. Style color — White, nearest to RHS NN155D. Stigma shape — Cleft, decurrent. Stigma length — 0.2 cm. Stigma diameter — 0.6 cm. Stigma color — White, nearest to RHS NN155C. Ovary color — Yellow-green, RHS 144C.

Seed and fruit: Not observed to date.

COMPARISONS WITH THE PARENT PLANT

Plants of the new cultivar 'LOSTE1517' may be distinguished from its seed parent, *Stevia* '3662/12', by the characteristics described in Table 1.

TABLE 1

| Characteristic | 'LOSTE1517' | '3662/12' |
|---|---|---|
| Plant habit. | More spreading than '3662/12'. | More erect than 'LOSTE1517'. |
| Rebaudioside A content in foliage, dry weight. | 59.8 mg/g. | 49.2 mg/g. |
| Stevioside content in foliage, dry weight. | 38.4 mg/g. | 43.4 mg/g. |
| Total steviol glycoside content of foliage, dry weight. | 106.8 mg/g. | 100.5 mg/g. |

Plants of the new cultivar 'LOSTE1517' may be distinguished from its pollen parent, *Stevia* '3668/12', by the characteristics described in Table 2.

TABLE 2

| Characteristic | 'LOSTE1517' | '3668/12' |
|---|---|---|
| Plant habit. | Less basal branching. | More basal branching. |
| Rebaudioside A content in foliage, dry weight. | 59.8 mg/g. | 29.8 mg/g. |
| Stevioside content in foliage, dry weight. | 38.4 mg/g. | 65.8 mg/g. |
| Total steviol glycoside content of foliage, dry weight. | 106.8 mg/g. | 104.5 mg/g. |

COMPARISON WITH THE MOST SIMILAR *STEVIA* CULTIVAR KNOWN TO THE INVENTOR

Plants of the new cultivar 'LOSTE1517' are most similar to the commercial variety, *Stevia rebaudiana* 'Candy' (not patented). A comparison of 'LOSTE1517' with 'Candy' is described in Table 3.

TABLE 3

| Characteristic | 'LOSTE1517' | 'Candy' |
|---|---|---|
| Phenotypical stability and uniformity. | More stable and. uniform | Less stable and less uniform. |
| Plant habit. | More compact. | Less compact. |
| Cold tolerance. | Foliage is more cold tolerant. | Foliage is more sensitive to cold temperatures. |
| Foliage size. | Larger than 'Candy'. | Smaller than 'LOSTE1517'. |
| Foliage color. | Darker green. | Lighter green. |
| Internode length. | Shorter than 'Candy'. | Longer than 'LOSTE1517'. |
| Rebaudioside A content in foliage, dry weight. | 18.7 mg/g. | 29.8 mg/g. |
| Stevioside content in foliage, dry weight. | 72.8 mg/g. | 65.8 mg/g. |
| Total steviol glycoside content of foliage, dry weight. | 94.8 mg/g. | 104.5 mg/g. |

That which is claimed is:

1. A new and distinct cultivar of *Stevia* plant named 'LOSTE1517', substantially as described and illustrated herein.

* * * * *